United States Patent
Boaz

(10) Patent No.: US 6,906,213 B1
(45) Date of Patent: Jun. 14, 2005

(54) PREPARATION OF AMINOPHOSPHINES

(75) Inventor: Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/876,492

(22) Filed: Jun. 25, 2004

(51) Int. Cl.[7] ............... C07F 17/02; B01J 31/00
(52) U.S. Cl. ............ 556/22; 556/144; 556/148; 502/162; 568/846
(58) Field of Search ............ 556/22, 144, 148; 564/12, 15; 502/162

(56) References Cited

U.S. PATENT DOCUMENTS 6,590,115 B2    7/2003    Boaz et al.

OTHER PUBLICATIONS

Schmidt et al, Synthesis, 1984, pp. 53–60.
Schmidt et al, Synthesis, 1992, pp. 487–490.

*Primary Examiner*—Porfirio Nazario-Gonzalez

(74) *Attorney, Agent, or Firm*—Michael J. Blake; Bernard J. Graves, Jr.

(57) ABSTRACT

Disclosed is a process for the preparation of phosphine-aminophosphines that are useful in the formation of catalysts useful in carrying out a wide variety of reactions such as asymmetric hydrogenations, asymmetric reductions, asymmetric hydroborations, asymmetric olefin isomerizations, asymmetric hydrosilations, asymmetric allylations, asymmetric conjugate additions, and asymmetric organometallic additions. The process comprises the steps of (1) contacting a compound of formula 2

$$R_2P\text{—}L\text{—}NHR^3 \qquad 2$$

with phosphorus trihalide $PX_3$ in the presence of an inert, organic solvent and an acid acceptor to produce intermediate compound having formula 3

$$R_2P\text{—}L\text{—}\underset{\underset{R^3}{|}}{N}\text{—}PX_2 \qquad 3$$

(2) contacting intermediate compound 3 with a reactant having the formula $R^1\text{—}M^1$, $R^2\text{—}M^1$ or a mixture thereof.

14 Claims, No Drawings

PREPARATION OF AMINOPHOSPHINES

FIELD OF THE INVENTION

This invention pertains to a novel process for the preparation of certain aminophosphines. More specifically, this invention pertains to a process for the preparation of phosphine-aminophosphines that are useful in the formation of catalysts useful in carrying out a wide variety of reactions such as asymmetric hydrogenations, asymmetric reductions, asymmetric hydroborations, asymmetric olefin isomerizations, asymmetric hydrosilations, asymmetric allylations, asymmetric conjugate additions, and asymmetric organometallic additions.

BACKGROUND OF THE INVENTION

Asymmetric catalysis is the most efficient method for the generation of products with high enantiomeric purity, as the asymmetry of the catalyst is multiplied many times over in the generation of the chiral product. These chiral products have found numerous applications as building bocks for single enantiomer pharmaceuticals as well as in some agrochemicals. The asymmetric catalysts employed can be enzymatic or synthetic in nature. The latter types of catalyst have much greater promise than the former due to much greater latitude of applicable reaction types. Synthetic asymmetric catalysts are usually composed of a metal reaction center surrounded by one or more organic ligands. The ligands usually are generated in high enantiomeric purity, and are the agents inducing the asymmetry. These ligands are in general difficult to make and therefore expensive. A notable exception are chiral phosphine-aminophosphine ligands which are readily prepared and air-stable, and have been described by Boaz, N. W. and Debenham, S. D., U.S. Pat. No. 6,590,115. The phosphine-aminophosphine compounds disclosed in U.S. Pat. No. 6,590,115 may be combined with catalytically-active metals to form complexes useful as catalysts in asymmetric hydrogenation processes. Compounds that may be obtained from such asymmetric hydrogenation processes are of great interest in the pharmaceutical industry and include, but are not limited to, amino acids, 2-substituted succinates, and 2-hydroxyesters having high enantiomeric purity.

U.S. Pat. No. 6,590,115 discloses the synthesis of phosphino-aminophosphines by a three-step process wherein (1) a dialkylamine-phosphine compound is reacted with a carboxylic acid anhydride to obtain the corresponding phosphine-ester compound;
(2) the phosphine-ester compound is reacted with a primary amine to obtain a secondary amine-phosphine compound; and
(3) the secondary amine-phosphine compound is reacted with a disubstituted phosphine halide.

The third step of the published synthesis of the phosphine-aminophosphine compounds involves the coupling of the precursor secondary amine-phosphine compound with a suitably substituted dialkyl, diaryl, or alkyl aryl phosphine halide. This method is limited by several factors. For example, there are only a limited number of chlorophosphines that are commercially available and the preparation of disubstituted phosphine halide is often arduous. In addition, coupling of the amine with the phosphine halide may be subject to severe steric constraints, which may limit the types of substituents that may be present on the nitrogen atom of the secondary amine-phosphine reactant and/or on the phosphorus atom of the disubstituted phosphine halide reactant.

BRIEF DESCRIPTION OF THE INVENTION

We have developed an improved process that permits the synthesis of a broad variety of phosphine-aminophosphine compounds. The process of the present invention provides for the preparation of a compound having formula 1:

$$R_2P-L-N(R^3)-PR^1R^2 \qquad 1$$

which comprises the steps of (1) contacting a compound of formula 2:

$$R_2P-L-NHR^3 \qquad 2$$

with a phosphorus trihalide $PX_3$ in the presence of an inert, organic solvent and an acid acceptor to produce intermediate compound having formula 3:

$$R_2P-L-\underset{\underset{R^3}{|}}{N}-PX_2 \qquad 3$$

and (2) contacting intermediate compound 3 with a reactant(s) having the formula $R^1-M^1$, $R^2-M^1$ or a mixture thereof;
wherein
R, $R^1$, $R^2$, and $R^3$ are the same or different and are selected from branched- or straight-chain $C_1$–$C_{20}$ alkyl, $C_3$–$C_8$ cycloalkyl, $C_6$–$C_{20}$ carbocyclic aryl, or $C_4$–$C_{20}$ heteroaryl wherein the heteroatoms are selected from sulfur, nitrogen, and oxygen;
L is a divalent chiral radical selected from branched- or straight-chain $C_1$–$C_{20}$ alkylene, $C_3$–$C_8$ cycloalkylene, $C_6$–$C_{20}$ carbocyclic arylene, $C_4$–$C_{20}$ heteroarylene wherein the heteroatoms are selected from sulfur, nitrogen, and oxygen, or metallocenylmethylene, wherein L is substantially enantiomerically pure, i.e., an enantiomeric excess of 90% or greater;
X is halide; and
$M^1$ is a metal selected from Group I and Group II metals including magnesium halide residues MgX of Grignard reactants $R^1$—MgX and $R^2$—MgX.

The skilled artisan will understand that any of the groups reflected by R, $R^1$, $R^2$, $R^3$ and L may be either substituted or unsubstituted.

DETAILED DESCRIPTION

Our novel process is carried out in an inert organic solvent. Examples include cyclic or acyclic ethers such as diethyl ether, diisopropyl ether, tert-butyl methyl ether and tetrahydrofuran (THF); aromatic hydrocarbons such as benzene, toluene, and xylene (including mixed xylene isomers); aliphatic and alicyclic hydrocarbons such as hexane, heptane, and cyclohexane; and mixtures of any two or more of the foregoing. The preferred solvent is toluene, xylenes, tert-butyl methyl ether, or tetrahydrofuran.

Step (1) is carried out in the presence of an acid acceptor, e.g., a compound that will react with and thus scavenge or consume the hydrogen halide generated by the reaction of step (1). The acid acceptor preferably is a $C_3$–$C_{15}$ tertiary amine or pyridine, with the preferred amines being triethylamine and diisopropylethylamine. The amount of acid acceptor present is typically about 1 to 5 moles, preferably about 1 to 2 moles, per mole of reactant 2.

The reactant 2 employed in step (1) may be obtained or made by a variety of methods, such as in U.S. Pat. No. 6,590,115. The relative amounts of reactant 2 and phosphorus trihalide $PX_3$ employed in step (1) typically provides a reactant 2 to phosphorus trihalide $PX_3$ mole ratio of about 0.5:1 to 4:1, preferably about 1:1 to 1.5:1. Although not expressly determined, results of subsequent reactions indicate that the intended dihaloaminophosphine 5 produced in this reaction (i.e., when L is a metallocenylmethylene) is substantially uncontaminated with monohalodiaminophosphine and triaminophosphine. This is surprising, as a statistical mixture of these species might be expected. Although not wishing to be bound by theory, these results may be due to the steric congestion engendered by the amine used which limits the number of amines that can react with the phosphorus trihalide. Phosphorus trihalide $PX_3$ may be any trihalide such as tifluoride, trichloride, tribromide or triiodide but preferably is phosphorus trichloride.

Step (1) of the process may be carried out at a temperature between about –100° C. and the boiling point of the inert, organic solvent, preferably at a temperature of about –80° C. to 60° C. Although it is not necessary to do so, dihalide intermediate 3 may be isolated before conducting the second step of the process.

In step (2) of the process intermediate 3 is contacted with one or more reactants having the formula $R^1$—$M^1$, $R^2$—$M^1$ or a mixture thereof in the presence of an inert, organic solvent (e.g., one or more of the solvents described above). The amounts of $R^1$—$M^1$ and/or $R^2$—$M^1$ employed normally provides a mole ratio of $R^1$—$M^1$/$R^2$—$M^1$ to phosphorus trihalide $PX_3$ used in step (1) of about 3:1 to 6:1, preferably about 3:1 to 4:1. Step (2) may be carried out at a temperature between about –100° C. and the boiling point of the solvent, preferably about –80° C. to 25° C. $M^1$ preferably is MgBr, MgCl, MgI, Li, Na, or K.

The product of the process having formula 1 may be isolated from the reaction mixture using methods known to those skilled in the art, e.g., by extraction, filtration, or crystallization. The product of formula 1 may be purified if necessary using conventional procedures such as extraction, chromatography, or crystallization.

The phosphinoamino-phosphine compounds prepared in accordance with the process of our invention preferably employ an L group that is a metallocenylmethylene, which provides a compound having formula 4 or 5 (the enantiomer of 4):

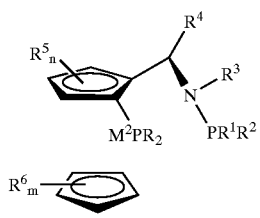

4

-continued

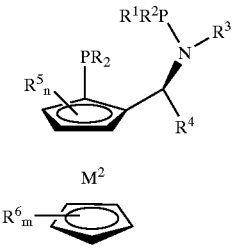

5 wherein

R, $R^1$, $R^2$ and $R^3$ are as defined above;

$R^4$, $R^5$, and $R^6$ are, independently, hydrogen, branched- or straight-chain $C_1$–$C_{20}$ alkyl, $C_3$–$C_8$ cycloalkyl, $C_6$–$C_{20}$ carbocyclic aryl, or $C_4$–$C_{20}$ heteroaryl wherein the heteroatoms are selected from sulfur, nitrogen, and oxygen;

n is 0 to 3;

m is 0 to 5; and $M^2$ is a metal from the metals of Groups IVB, VB, VIB, VIIB or VIII. A particularly preferred group of phosphinoamino-phosphine compounds that may be synthesized in accordance with our invention have formulas 4 and 5 wherein R is aryl, most preferably phenyl; $R^1$ and $R^2$ are the same substituents selected from aryl, $C_2$–$C_6$ alkyl, or $C_3$–$C_6$ cycloalkyl, most preferably phenyl, p-methoxyphenyl, 3,4-difluorophenyl, 3,5-difluorophenyl, 3,4-dichlorophenyl, 3,5-dichlorophenyl, 3-fluorophenyl, or 4-fluorophenyl; $R^3$ is hydrogen, $C_1$ to $C_6$ alkyl, or aryl; $R^4$ is hydrogen, $C_1$ to $C_6$ alkyl, benzyl, racemic or substantially enantiomerically pure 1-phenylethyl, or aryl; $R^5$ and $R^6$ are hydrogen; and $M^2$ is iron, ruthenium, or osmium, most preferably iron. The skilled artisan will understand that any of the groups reflected by $R^4$, $R^5$ and $R^6$ may be either substituted or unsubstituted.

The alkyl groups which may be represented by each of R, $R^1$, $R^2$, $R^3$, $R^4$, $R^5$, $R^6$, and L may be straight- or branched-chain aliphatic hydrocarbon radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, aryl and halogen. The terms "$C_1$–$C_6$-alkoxy", "$C_2$–$C_6$-alkoxycarbonyl", and "$C_2$–$C_6$-alkanoyloxy" are used to denote radicals corresponding to the structures —$OR^7$, —$CO_2R^7$, and —$OCOR^7$, respectively, wherein $R^7$ is $C_1$–$C_6$-alkyl or substituted $C_1$–$C_6$-alkyl. The term "$C_3$–$C_8$-cycloalkyl" is used to denote a saturated, carbocyclic hydrocarbon radical having three to eight carbon atoms. The aryl groups which each of R, $R^1$, $R^2$, $R^3$, $R^4$, $R^5$, $R^6$, and L may represent may include phenyl, naphthyl, or anthracenyl and phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, cyano, $C_1$–$C_6$-alkanoyloxy, $C_1$–$C_6$-alkylthio, $C_1$–$C_6$-alkylsulfonyl, trifluoromethyl, $C_2$–$C_6$-alkoxycarbonyl, $C_2$–$C_6$-alkanoylamino and —O—$R^8$, S—$R^8$, —$SO_2$—$R^8$, —$NHSO_2R^8$ and —$NHCO_2R^8$, wherein $R^8$ is phenyl, naphthyl, or phenyl or naphthly substituted with one to three groups selected from $C_1$–$C_6$-alkyl, $C_6$–$C_{10}$ aryl, $C_1$–$C_6$-alkoxy and halogen.

The $C_4$–$C_{20}$ heteroaryl radicals described herein include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl and $C_2$–$C_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

The skilled artisan will understand that each of the references herein to groups or moieties having a stated range of carbon atoms, such as "$C_1$–$C_6$-alkyl," includes not only the $C_1$ group (methyl) and $C_6$ group (hexyl) end points, but also each of the corresponding individual $C_2$, $C_3$, $C_4$ and $C_5$ groups. In addition, it will be understood that each of the individual points within a stated range of carbon atoms may be further combined to describe subranges that are Inherently within the stated overall range. For example, the term "$C_1$–$C_6$-alkyl" includes not only the individual moieties $C_1$ through $C_6$, but also contemplates subranges such as "$C_2$–$C_5$-alkyl."

Complexes of the phosphine-aminophosphine compounds of formula 1 with a catalytically-active metal ("metal") are effective catalysts for promoting a large number of possible reactions employing a wide variety of reactants. Examples of possible reactions include asymmetric hydrogenations, asymmetric reductions, asymmetric hydroborations, asymmetric olefin isomerizations, asymmetric hydrosilations, asymmetric allylations, asymmetric conjugate additions and asymmetric organometallic additions. The particular metal selected for complexation with the phosphine-aminophosphine compounds of formula 1 depends on the desired reaction. The metal may be selected from Group VIII metals with iridium, ruthenium and, especially, rhodium being preferred. Although the complexes may be prepared and isolated prior to use, it is preferable to prepare the complex in situ from phosphine-aminophosphine compound 1 and a metal pre-catalyst. The relative amounts of phosphine-aminophosphine compound 1 and catalytically-active metal employed typically provide a phosphorus:metal atomic ratio of about 1:1 to about 4:1, preferably about 2:1 to 3:1.

The complexes of the phosphine-aminophosphine compounds of formula 1 with a catalytically-active metal are especially useful in performing asymmetric hydrogenation reactions which constitutes another embodiment of our invention. Thus, the present invention includes a process for the hydrogenation of a hydrogenatable compound which comprises contacting the hydrogenatable compound with hydrogen in the presence of a catalyst complex of a phosphine-aminophosphine compound of formula 1 with a catalytically-active metal under hydrogenation conditions of temperature and pressure. For asymmetric hydrogenation reactions, the catalytically-active metal complexed preferably is rhodium, iridium, or ruthenium, and most preferably is rhodium. The amount of complex utilized in the hydrogenation process may vary between about 0.00005 and 0.5 molar equivalents based on the reactant compound, with more complex usually providing faster reaction rates. The reaction atmosphere is hydrogen, but may also contain other materials that are inert to the reaction conditions. The reaction can be run at atmospheric pressure or at elevated pressure, e.g., from about 0.5 to 200 bars gauge (barg). The reaction is run at a temperature which affords a reasonable rate of conversion, which can be as low as −50° C. but is usually between ambient temperature and the boiling point (or apparent boiling point at elevated pressure) of the lowest boiling component of the reaction mixture.

EXAMPLES

The process provided by the present invention and the use of the phosphine-aminophosphine compounds obtained from the process are further illustrated by the following examples.

Example 1

Preparation of (R)-N-diphenylphosphino-N-methyl-1-[(S)-2-(diphenylphosphino)ferrocenyl]ethylamine (4a)

Toluene (10 mL) was added to a 100mL 3-necked flask which was cooled in ice to below 5° C. Phosphorus trichloride (0.26 mL; 3.0 mmol; 1.0 equiv based on 2a) was added followed by triethylamine (0.50 mL; 3.6 mmol; 1.2 equiv). (R)-N-methyl-1-[(S)-2-(diphenylphosphino)ferrocenyl] ethylamine (2a)(1.26 g; 3.0 mmol) dissolved in 10 mL of toluene was added over about 5 minutes such that the temperature remained below 10° C. The reaction mixture was allowed to warm to ambient temperature over 30 min and stirred at ambient temperature for 2 hours. The reaction mixture was cooled in ice to below 5° C. and a 3.0 M solution of phenylmagnesium bromide in diethyl ether (3.5 mL; 10.5 mmol; 3.5 equiv) was added over approximately 10 minutes such that the temperature remained below 10° C. The reaction mixture was allowed to warm to ambient temperature overnight to completely consume 2a according to thin layer chromatography (tlc) analysis. The mixture was cooled in ice-water and saturated aqueous sodium bicarbonate solution (20 mL) was added at a rate such that the temperature remained below 15° C. The layers were separated, the aqueous solution was filtered to remove insolubles, and it was further extracted with ethyl acetate. The combined organic extracts were dried with sodium sulfate and concentrated. The crude product was filtered through a pad of neutral alumina and eluted with 1:9 ethyl acetate:heptane with 5% added triethylamine to afford 1.52 g (83%) of 4a.

$^1$H NMR (CDCl$_3$) δ 7.65 (m, 2H); 7.4–7.0 (m, 14H); 6.82 (m, 4H); 5.006 (m, 1H); 4.502 (br s, 1H); 4.40 (m, 1H); 4.15 (m, 1H); 3.798 (s, 5H); 2.148 (d, 3H, J=3.30 Hz); 1.471 (d, 3H, J=6 87 Hz). FDMS: m/z 611 (M$^+$). [α]$_D^{25}$+229.8° (c 1.10, toluene).

Example 2

Preparation of (R)-N-diphenylphosphino-N-isopropyl-1-[(S)-2-(diphenylphosphino)ferrocenyl] ethylamine (4b)

Toluene (10 mL) was added to a 100-mL 3-necked flask which was cooled to below −70° C. in a dry ice-acetone bath. Phosphorus trichloride (174 µL; 2.0 mmol; 1.0 equiv based on 2b) was added followed by triethylamine (0.33 mL; 2.4 mmol; 1.2 equiv). (R)-N-Isopropyl-1-[(S)-2-(diphenylphosphino)ferrocenyl]ethylamine (2b)(910 mg; 2.0 mmol) dissolved in 8 mL of toluene was added dropwise such that the temperature remained below −50° C. The reaction mixture was stirred in dry ice-acetone for 1 hour, then allowed to warm to ambient temperature over 1 hour and stirred at ambient temperature for 2 hours. The reaction mixture was cooled to below −70° C. and a 3.0 M solution of phenylmagnesium bromide in diethyl ether (2.33 mL; 7.0 mmol; 3.5 equiv) was added such that the temperature remained below −50° C. The reaction mixture was allowed to warm to ambient temperature overnight to completely consume 2b according to tlc analysis. Heptane (25 mL) was added and the reaction mixture was quenched by the addition of acetone (0.78 mL; 5 equiv). The mixture was filtered, the precipitate was washed with ethyl acetate, and the filtrate was stripped. The residue was dissolved in hot ethyl acetate, filtered and stripped to afford 0.95 g of crude product. This material was filtered through a pad of neutral alumina and eluted with 1:9 ethyl acetate:heptane with 5% added triethylamine to afford 0.86 g (67%) of 4b. This material was further purified by trituration with hot ethyl acetate, dilution with heptane and cooling to ambient temperature. The resulting precipitate was filtered, washed with heptane, and dried to afford 560 mg (44%) of 4b.

$^1$H NMR (CDCl$_3$) δ 7.5–7.0 (m, 20H); 4.828 (br s, 1H); 4.289 (m, 1H); 4.016 (s, 5H); 3.95 (m, 1H); 3.718 (br s, 1H); 3.6 (m, 1H); 1.56 (m, 3H); 1.085 (m, 3H); 0.876 (m, 3H). FDMS: m/z 639.2 (M$^+$).

Example 3

Preparation of (R)-N-diphenylphosphino-N-neopentyl-1-[(S)-2-(diphenylphosphino)ferrocenyl]ethylamine (4c)

Toluene (10 mL) was added to a 100-mL 3-necked flask which was cooled to below −70° C. in a dry ice-acetone bath. Phosphorus trichloride (174 μL; 2.0 mmol; 1.0 equiv based on 2c) was added followed by triethylamine (0.33 mL; 2.4 mmol; 1.2 equiv). (R)-N-Neopentyl-1-[(S)-2-(diphenylphosphino)ferrocenyl]ethylamine (2c)(967 mg; 2.0 mmol) dissolved in 8 mL of toluene was added dropwise such that the temperature remained below −50° C. The reaction mixture was stirred in dry ice-acetone for 1 hour, then allowed to warm to ambient temperature over 1 hour and stirred at ambient temperature for 2 hours. The reaction mixture was cooled to below −70° C. and a 3.0 M solution of phenylmagnesium bromide in diethyl ether (2.33 mL; 7.0 mmol; 3.5 equiv) was added such that the temperature remained below −50° C. The reaction mixture was allowed to warm to ambient temperature overnight to completely consume 2c according to tlc analysis. Heptane (25 mL) was added and the reaction mixture was quenched by the addition of acetone (0.78 mL; 5 equiv). The mixture was filtered through celite, the precipitate was washed with ethyl acetate, and the filtrate was stripped. The residue was dissolved in hot ethyl acetate, filtered and stripped to afford 1.57 g of crude product. This material was filtered through a pad of flash silica gel and eluted with 1:9 ethyl acetate:heptane with 5% added triethylamine to afford 0.74 g. This material was dissolved in hot ethyl acetate, diluted with heptane and cooled to 4° C. overnight. The resulting crystals were filtered, washed with heptane, and dried to afford 170 mg (13%) of 4c.

$^1$H NMR (CDCl$_3$) δ 7.70 (m, 2H); 7.562 (t, 2H, J=6.87 Hz); 7.45–7.1 (m, 14H); 6.75 (m, 2H); 4.840 (br s,1H); 4.6 (m, 1H); 4.215 (m, 1H); 4.177 (br s, 1H); 3.837 (s, 5H); 2.386 (d, 1H, J=14.56 Hz); 2.242 (dd, 1H, J=4.40, 14.56 Hz); 2.074 (d, 3H, J=6.59 Hz); 0.312 (s, 9H). FDMS: m/z 667.17 (M$^+$).

Example 4

Preparation of (R)-N-diphenylphosphino-N-tert-butyl-1-[(S)-2-(diphenylphosphino)ferrocenyl]ethylamine (4d)

Toluene (5 mL) was added to a 100-mL 3-necked flask which was cooled to <5° C. in an ice bath. Phosphorus trichloride (240 μL; 2.75 mmol; 1.0 equiv based on 2d) was added followed by triethylamine (0.46 mL; 3.3 mmol; 1.2 equiv). (R)-N-tert-Butyl-1-[(S)-2-(diphenylphosphino)ferrocenyl]ethylamine (2d)(1.29 g; 2.75 mmol) dissolved in 8 mL of toluene was added dropwise such that the temperature remained below 10° C. and washed in with 2 mL of toluene. The reaction mixture was heated to 50° C. for 24 hours, then was cooled to <5° C. and a 3.0 M solution of phenylmagnesium bromide in diethyl ether (3.20 mL; 9.6 mmol; 3.5 equiv) was added such that the temperature remained below 15° C. The reaction mixture was allowed to warm to ambient temperature overnight. The mixture was cooled in ice-water and heptane (20 mL) was added. Saturated aqueous sodium bicarbonate solution (10 mL) was added at a rate such that the temperature remained below 10° C. The layers were separated, the aqueous solution was filtered to remove insolubles, and it was extracted twice with ethyl acetate. The combined organic extracts were dried with magnesium sulfate and concentrated. The crude product was filtered through a pad of flash silica gel and eluted with 1:9 ethyl acetate:heptane with 5% added triethylamine to afford 0.88 g (49%) of 4d.

$^1$H NMR (CDCl$_3$) δ 7.7–7.1 (m, 20H); 4.962 (br s, 1H); 4.55–4.4 (m, 1H); 4.230 (m, 1H); 3.897 m, 1H); 3.867 (s, 5H); 2.222 (br s, 3H); 0.962 (br s, 9H). FDMS: m/z 653.77 (M$^+$).

Example 5

Preparation of (R)-N-diphenylphosphino-N-phenyl-1-[(S)-2-(diphenylphosphino)ferrocenyl]ethylamine (4e)

Toluene (5 mL) was added to a 100-mL 3-necked flask which was cooled to <5° C. in an ice bath. Phosphorus trichloride (200 μL; 2.29 mmol; 1.0 equiv based on 2e) was added followed by triethylamine (0.38 mL; 2.75 mmol; 1.2 equiv). (R)-N-Phenyl-1-[(S)-2-(diphenylphosphino)ferrocenyl]ethylamine (2e)(1.12 g; 2.29 mmol) dissolved in 8 mL of toluene was added dropwise such that the temperature remained below 10° C. and washed in with 2 mL of toluene. The reaction mixture was warmed to ambient temperature for 24 hours, then was cooled to <5° C. and a 3.0 M solution of phenylmagnesium bromide in diethyl ether (2.70 mL; 8.0 mmol; 3.5 equiv) was added such that the temperature remained below 15° C. The reaction mixture was allowed to warm to ambient temperature overnight. The mixture was cooled in ice-water and heptane (20 mL) was added. Saturated aqueous sodium bicarbonate solution (10 mL) was added at a rate such that the temperature remained below 10° C. The layers were separated, the aqueous solution was filtered to remove insolubles, and it was extracted twice with ethyl acetate. The combined organic extracts were dried with magnesium sulfate and concentrated to afford 1.56 g of crude product. This material was filtered through a pad of flash silica gel and eluted with 1:9 ethyl acetate:heptane with 5% added triethylamine to afford 1.19 g (77%) of 4e.

$^1$H NMR (CDCl$_3$) δ 7.7–7.0 (m, 20H); 6.74 (m, 3H); 6.47 (m, 2H); 5.35 (m, 1H); 4.571 (br s, 1H); 4.358 (m, 1H); 4.115 (br s,1H); 3.865 (s, 5H); 1.997 (d, 3H, J=6.87 Hz). FDMS: m/z 673.77 (M$^+$).

Example 6

Preparation of (R)-N-diphenylphosphino-N-benzyl-1-[(S)-2-(diphenylphosphino)ferrocenyl]ethylamine (4f)

Toluene (5 mL) was added to a 100-mL 3-necked flask which was cooled to <5° C. in an ice bath. Phosphorus trichloride (234 μL; 2.68 mmol; 1.0 equiv based on 2f) was added followed by triethylamine (0.45 mL; 3.22 mmol; 1.2 equiv). (R)-N-Benzyl-1-[(S 2-(diphenylphosphino) ferrocenyl]ethylamine (2f)(1.35 9; 2.68 mmol) dissolved in 10 mL of toluene was added dropwise such that the temperature remained below 10° C. and washed in with 2 mL of toluene. The reaction mixture was stirred at <5° C. for 45 min, warmed to ambient temperature for 2 h, then was cooled to <5° C. and a 3.0 M solution of phenylmagnesium bromide in diethyl ether (3.15 mL; 9.4 mmol; 3.5 equiv) was added such that the temperature remained below 15° C. The reaction mixture was allowed to warm to ambient temperature overnight. The mixture was cooled in ice-water and heptane (20 mL) was added. Saturated aqueous sodium bicarbonate solution (10 mL) was added at a rate such that the temperature remained below 10° C. The layers were separated, the aqueous solution was filtered to remove insolubles, and it was extracted twice with ethyl acetate. The combined organic extracts were dried with magnesium sulfate and concentrated, and the crude product was filtered through a pad of neutral alumina and eluted with 1:9 ethyl acetate:heptane with 5% added triethylamine to afford a center cut of 1.18 g (64%) of 4f.

$^1$H NMR (CDCl$_3$) δ 7.60–7.58 (m, 2H); 7.5–7.1 (m, 19H); 6.941 (t, 2H, J=6.59 Hz); 6.74 (m, 2H); 4.826 (br s, 1H); 4.386 (m, 1H); 4.35 (m, 1H); 4.185 (br s, 1H); 3.752 (s, 5H); 3.697 (s, 2H); 1.804 (d, 3H, J=7.14 Hz).

Example 7

Preparation of (R)-N-diphenylphosphino-N-[(S)-1-phenylethyl-1-[(S)-2-(diphenylphosphino) ferrocenyl]ethylamine (4g)

Toluene (5 mL) was added to a 100-mL 3-necked flask which was cooled to <5° C. in an ice bath. Phosphorus trichloride (131 μL; 1.50 mmol; 1.0 equiv based on 2 g) was added followed by triethylamine (0.25 mL; 1.80 mmol; 1.2 equiv). (R)-N-[(S)-1-Phenylethyl]-1-[(S)-2-(diphenylphosphino)ferrocenyl]ethylamine (2 g)(776 mg; 1.5 mmol) dissolved in 8 mL of toluene was added dropwise such that the temperature remained below 10° C. and washed in with 2 mL of toluene. The reaction mixture was allowed to warm to ambient temperature for one hour and stirred at ambient temperature for 6 hours, then was cooled to <5° C. and a 3.0 M solution of phenylmagnesium bromide in diethyl ether (1.75 mL; 5.25 mmol; 3.5 equiv) was added such that the temperature remained below 10° C. The reaction mixture was allowed to warm to ambient temperature overnight. The mixture was cooled in ice-water and heptane (15 mL) was added. Saturated aqueous sodium bicarbonate solution (10 mL) was added at a rate such that the temperature remained below 10° C. The layers were separated, the aqueous solution was filtered to remove insolubles, and it was extracted with ethyl acetate. The combined organic extracts were dried with magnesium sulfate and concentrated to afford 1.17 g of crude product. This material was filtered through a pad of neutral alumina and eluted with 5:5:90 ethyl acetate:triethylamine:heptane to afford 789 mg (75%) of 4 g.

$^1$H NMR (CDCl$_3$) δ 7.6–7.0 (m, 25H); 4.69 (m, 2H); 4.216 (m, 1H); 4.15 (m, 1H); 4.031 (s, 5H); 1.493 (d, 3H, J=6.59 Hz); 1.45 (m, 3H).

Example 8

Preparation of (R)-N-diphenylphosphino-N-[(R)-1-phenylethyl]-1-[(S)-2-(diphenylphosphino) ferrocenyl]ethylamine (4h)

Toluene (10 mL) was added to a 100-mL 3-necked flask which was cooled to <5° C. in an ice bath. Phosphorus trichloride (218 μL; 2.50 mmol; 1.0 equiv based on 2h) was added followed by triethylamine (0.42 mL; 3.0 mmol; 1.2 equiv). (R)-N-[(R)-1-Phenylethyl]-1-[(S)-2-(diphenylphosphino)ferrocenyl]ethylamine (2h)(1.29 g; 2.50 mmol) dissolved in 8 mL of toluene was added dropwise such that the temperature remained below 10° C. and washed in with 2 mL of toluene. The reaction mixture was allowed to warm to ambient temperature for one hour and stirred at ambient temperature for 27 hours, then was cooled to <5° C. and a 3.0 M solution of phenylmagnesium bromide in diethyl ether (2.90 mL; 8.73 mmol; 3.5 equiv) was added such that the temperature remained below 10° C. The reaction mixture was allowed to warm to ambient temperature overnight. The mixture was cooled in ice-water and heptane (20 mL) was added. Saturated aqueous sodium bicarbonate solution (10 mL) was added at a rate such that the temperature remained below 10° C. The mixture was filtered to remove insolubles, the layers were separated, and the aqueous layer was extracted with ethyl acetate. The combined organic extracts were dried with magnesium sulfate and concentrated to afford 2.11 g of crude product This material was filtered through a pad of neutral alumina and eluted with 5:5:90 ethyl acetate:triethylamine:heptane to afford 1.60g of 4h. This material was dissolved in 16 mL of refluxing tert-butanol and cooled to ambient temperature, at which point solid was noted. Water (16 mL) was added to afford significantly more solid. This mixture was allowed to stand for 30 minutes, filtered, and washed with water. The resulting solid was dried under vacuum with a nitrogen sweep to afford 1.46 g (83%) of 4h.

$^1$H NMR (CDCl$_3$) δ 7.6–7.0 (m, 23H); 6.915 (t, 2H, J=7.14 Hz); 4.93 (m, 1H); 4.347 (s, 1H); 4.116 (s, 5H); 4.064 (m, 1H); 3.812 (m(5), 1H, J=5.77 Hz); 3.426 (s, 1H); 1.685 (m, 3H); 1.378 (m, 3H).

Example 9

Preparation of (R)-N-[bis(4-methoxyphenyl) phosphino]-N-methyl-1-[(S)-2-diphenylphosphino) ferrocenyl]ethylamine (4i)

Toluene (10 mL) was added to a 100-mL 3-necked flask which was cooled to <5° C. in an ice bath. Phosphorus trichloride (174 μL; 2.0 mmol; 1.0 equiv based on 2a) was added followed by triethylamine (0.33 mL; 2.4 mmol; 1.2 equiv). (R)-N-Methyl-1-[(S)-2-(diphenylphosphino) ferrocenyl]ethylamine (2a)(855 mg; 2.0 mmol) dissolved in 8 mL of toluene was added dropwise such that the temperature remained below 10° C. and washed in with 2 mL of toluene. The reaction mixture was warmed to ambient temperature for 2 hours, then was cooled to <5° C. and a 0.5 M solution of 4-methoxyphenylmagnesium bromide in THF (14 mL; 7.0 mmol; 3.5 equiv) was added over about 10 minutes such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The layers were separated, the aqueous solution was filtered to remove insolubles, and it was extracted twice with ethyl acetate. The combined organic extracts were dried with sodium sulfate and concentrated to afford 1.56 g of crude product. This material was filtered through a pad of neutral alumina and eluted with a gradient of from 1:9 to 1:4 ethyl acetate:heptane with 5% added triethylamine to afford 0.17 g of pure 2f and 1.10 g of impure material. The latter was dissolved in 5 mL of refluxing tert-butanol and allowed to cool to ambient temperature. The resulting precipitate was collected by filtration, washed with tert-butanol, and dried to afford 0.81 g (total yield 73%) of 4i.

FDMS: m/z 671.03 (M$^+$).

Example 10

Preparation of (R)-N-[bis(3,4-difluorophenyl)phosphino]-N-methyl-1[(S)-2-diphenylphosphino)ferrocenyl]ethylamine (4j)

Toluene (10 mL) was added to a 100-mL 3-necked flask which was cooled to <5° C. in an ice bath. Phosphorus trichloride (174 μL; 2.0 mmol; 1.0 equiv based on 2a) was added followed by triethylamine (0.33 mL; 2.4 mmol; 1.2 equiv). (R)-N-Methyl-1-[(S)-2-(diphenylphosphino)ferrocenyl]ethylamine (2a)(855 mg; 2.0 mmol) dissolved in 8 mL of toluene was added dropwise such that the temperature remained below 5° C. and washed in with 2 mL of toluene. The reaction mixture was stirred below 5° C. for 30 minutes and warmed to ambient temperature for 1 hour, then was cooled to <5° C. and a 0.5 M solution of 3,4-difluorophenylmagnesium bromide in THF (14 mL; 7.0 mmol; 3.5 equiv) was added over about 10 min such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The layers were separated, the aqueous solution was filtered to remove insolubles, and it was extracted twice with ethyl acetate. The combined organic extracts were dried with sodium sulfate and concentrated to afford 1.79 g of crude product. This material was filtered through a pad of neutral alumina and eluted with 1:9 ethyl acetate-:heptane with 5% added triethylamine to afford 1.40 g of 4j. This material was dissolved in 7.5 mL of refluxing tert-butanol, allowed to cool to ambient temperature, and diluted with 7.5 mL of water. The mixture was then cooled to 4° C. for 6 h, and the resulting precipitate was collected by filtration, washed with water, and dried to afford 1.33 g of about 86% assay 4j (84% yield), with the balance being tert-butanol.

$^1$H NMR (CDCl$_3$) δ 7.65 (m, 3H); 7.5–7.0 (m, 10H); 6.7–6.5 (m, 3H); 4.98 (m, 1H); 4.517 (brs, 1H); 4.432 (m, 1H); 4.168 (brs, 1H); 3.797 (s, 5H); 2.163 (d, 3H, J=3.57 Hz); 1.499 (d, 3H, J=6.87 Hz). FDMS: m/z 683.03 (M$^+$).

Example 11

Preparation of (R)-N-[bis(3,4-dichlorophenyl)phosphino]-N-methyl-1-[(S)-2-diphenylphosphino)ferrocenyl]ethylamine (4k)

Toluene (10 mL) was added to a 100-mL 3-necked flask which was cooled to <5° C. in an ice bath. Phosphorus trichloride (174 μL; 2.0 mmol; 1.0 equiv based on 2a) was added followed by triethylamine (0.33 mL; 2.4 mmol; 1.2 equiv). (R)-N-Methyl-1-[(S)-2-(diphenylphosphino)ferrocenyl]ethylamine (2a)(855 mg; 2.0 mmol) dissolved in 8 mL of toluene was added dropwise such that the temperature remained below 5° C. and washed in with 2 mL of toluene. The reaction mixture was stirred below 5° C. for 30 minutes and warmed to ambient temperature for 1 hour, then was cooled to <5° C. and a 0.5 M solution of 3,4-dichlorophenylmagnesium bromide in THF (14 mL; 7.0 mmol; 3.5 equiv) was added over about 10 min such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The layers were separated, the aqueous solution was filtered to remove insolubles, and it was extracted twice with ethyl acetate. The combined organic extracts were dried with sodium sulfate and concentrated to afford 2.16 g of crude product. This material was filtered through a pad of neutral alumina and eluted with 1:9 ethyl acetate-:heptane with 5% added triethylamine to afford 1.45 g of 4k (97%).

$^1$H NMR (CDCl$_3$) δ 7.7–6.6 (m, 16H); 4.93 (m, 1H); 4.538 (br s, 1H); 4.443 (m, 1H); 4.173 (br s, 1H); 3.795 (s, 5H); 2.178 (d, 3H, J=3.30 Hz); 1.543 (d, 3H, J=6.87 Hz).

Example 12

Preparation of (R)-N-[bis(3,5-difluorophenyl)phosphino]-N-methyl-1-[(S)-2-diphenylphosphino)ferrocenyl]ethylamine (4m)

Toluene (10 mL) was added to a 100-mL 3-necked flask which was cooled to <5° C. in an ice bath. Phosphorus trichloride (174 μL; 2.0 mmol; 1.0 equiv based on 2a) was added followed by triethylamine (0.33 mL; 2.4 mmol; 1.2 equiv). (R)-N-Methyl-1-[(S)-2-(diphenylphosphino)ferrocenyl]ethylamine (2a)(855 mg; 2.0 mmol) dissolved in 8 mL of toluene was added dropwise such that the temperature remained below 5° C. and washed in with 2 mL of toluene. The reaction mixture was stirred below 5° C. for 30 minutes and warmed to ambient temperature for 3 hours, then was cooled to <5° C. and a 0.5 M solution of 3,5-difluorophenylmagnesium bromide in THF (14 mL; 7.0 mmol; 3.5 equiv) was added over about 10 min such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The layers were separated, the aqueous solution was filtered to remove insolubles, and it was extracted twice with ethyl acetate. The combined organic extracts were dried with magnesium sulfate and concentrated to afford 1.70 g of crude product. This material was filtered through a pad of neutral alumina and eluted with 1:9 ethyl acetate:heptane with 5% added triethylamine to afford 1.10 g of 4m (80%).

$^1$H NMR (CDCl$_3$) δ 7.63 (m, 2H); 7.385 (br s, 4H); 7.2–7.0 (m, 6H); 6.75–6.6 (m, 2H); 6.6–6.4 (m, 2H); 4.88 (m, 1H); 4.566 (br s, 1H); 4.445 (m, 1H); 4.170 (br s, 1H); 3.806 (s, 5H); 2.241 (d, 3H, J=3.30 Hz); 1.590 (d, 3H, J=6.87 Hz).

Example 13

Preparation of (R)-N-[bis(3,5-dichlororophenyl)phosphino]-N-methyl-1-[(S)-2-diphenylphosphino)ferrocenyl]ethylamine (4n)

Toluene (10 mL) was added to a 100-mL 3-necked flask which was cooled to <5° C. in an ice bath. Phosphorus trichloride (174 μL; 2.0 mmol; 1.0 equiv based on 2a) was added followed by triethylamine (0.33 mL; 2.4 mmol; 1.2 equiv). (R)-N-Methyl-1-[(S)-2-(diphenylphosphino) ferrocenyl]ethylamine (2a)(855 mg; 2.0 mmol) dissolved in 8 mL of toluene was added dropwise such that the temperature remained below 5° C. and washed in with 2 mL of toluene. The reaction mixture was stirred below 5° C. for 30 minutes and warmed to ambient temperature for 3 hours, then was cooled to <5° C. and a 0.5 M solution of 3,5-dichlorophenylmagnesium bromide in THF (14 mL; 7.0 mmol; 3.5 equiv) was added over about 15 min such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The layers were separated, the aqueous solution was filtered to remove insolubles, and it was extracted twice with ethyl acetate. The combined organic extracts were dried with magnesium sulfate and concentrated to afford 1.98 g of crude product. This material was filtered through a pad of neutral alumina and eluted with 1:9 ethyl acetate:heptane with 5% added triethylamine to afford 1.08 g of 4n (97%). This material was triturated with 10 mL of refluxing tert-butanol, cooled to ambient temperature. and diluted with 10 mL of water. The resulting gummy solid was collected, washed with water, and dried under vacuum with a nitrogen sweep to afford 0.87 g (58%) of 4n.

$^1$H NMR (CDCl$_3$) δ 7.7–6.9 (m, 16H); 4.80 (m, 1H); 4.597 (brs, 1H); 4.462 (m, 1H); 4.164 (br s,1H); 3.800 (s, 5H); 2.262 (d, 3H, J=3.02 Hz); 1.655 (d, 3H, J=6.87 Hz).

Example 14

Preparation of (R)-N-[bis(4-fluorophenyl) phosphino]-N-methyl-1-[(S)-2-diphenylphosphino) ferrocenyl]ethylamine (4o)

Toluene (10 mL) was added to a 100-mL 3-necked flask which was cooled to <5° C. in an ice bath. Phosphorus trichloride (0.26 mL; 3.0 mmol; 1.0 equiv based on 2a) was added followed by triethylamine (0.50 mL; 3.6 mmol; 1.2 equiv). (R)-N -Methyl-1-[(S)-2-(diphenylphosphino) ferrocenyl]ethylamine (2a)(1.28 9; 3.0 mmol) dissolved in 10 mL of toluene was added dropwise such that the temperature remained below 5° C. and washed in with 2 mL of toluene. The reaction mixture was stirred below 5° C. for 30 minutes and warmed to ambient temperature for 2 hours, then was cooled to <5° C. and a 2.0 M solution of 4-fluorophenylmagnesium bromide in diethyl ether (5.25 mL; 10.5 mmol; 3.5 equiv) was added slowly dropwise such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The mixture was filtered to remove insolubles and the layers were separated. The aqueous solution was extracted once with ethyl acetate. The combined organic extracts were dried with magnesium sulfate and concentrated, and the crude product was filtered through a pad of neutral alumina and eluted with 1:9 ethyl acetate:heptane with 5% added triethylamine to afford 1.58 g of 4o (81%).

$^1$H NMR (CDCl$_3$) δ7.64 (m, 2H); 7.4–7.15 (m, 8H); 7.080 (t, 2H, J=6.59 Hz); 6.963 (t, 2H, J=8.79 Hz); 6.72 (m, 2H); 6.521 (t, 2H, J=8.52 Hz); 5.01 (m, 1H); 4.485 (br s, 1H); 4.409 (m, 1H); 4.157 (br s,1H); 3.795 (s, 5H); 2.110 (d, 3H, J=3.57 Hz); 1.436 (d,3H, J=6.87 Hz).

Example 15

Preparation of (R)-N-[bis(3-fluorophenyl) phosphino]-N-methyl-1-[(S)-2-diphenylphosphino) ferrocenyl]ethylamine (4p)

Toluene (10 mL) was added to a 100-mL 3-necked flask which was cooled to <5° C. in an ice bath. Phosphorus trichloride (0.26 mL; 3.0 mmol; 1.0 equiv based on 2a) was added followed by triethylamine (0.50 mL; 3.6 mmol; 1.2 equiv). (R)-N -Methyl-1-[(S)-2-(diphenylphosphino) ferrocenyl]ethylamine (2a)(1.28 g; 3.0 mmol) dissolved in 10 mL of toluene was added dropwise such that the temperature remained below 5° C. and washed in with 2 mL of toluene. The reaction mixture was stirred below 5° C. for 30 minutes and warmed to ambient temperature for 2 hours, then was cooled to <5° C. and a 1.0 M solution of 3-fluorophenylmagnesium bromide in THF (10.5 mL; 10.5 mmol; 3.5 equiv) was added slowly dropwise such that the temperature remained below 10° C. The reaction mixture was allowed to warm to ambient temperature overnight to completely consume 2a according to tlc analysis. The mixture was cooled in ice-water and heptane (20 mL) was added. Saturated aqueous sodium bicarbonate solution (15 mL) was added at a rate such that the temperature remained below 10° C. The mixture was filtered to remove insolubles and the layers were separated. The aqueous solution was extracted once with ethyl acetate. The combined organic extracts were dried with magnesium sulfate and concentrated to afford 2.28 g of crude product. This material was filtered through a pad of neutral alumina and eluted with 1:9 ethyl acetate:heptane with 5% added triethylamine to afford 1.71 g of 4p (88%). This material was dissolved in 17 mL of refluxing tert-butanol and cooled to ambient temperature to afford solid. Water (17 mL) was added, resulting in much additional solid. The mixture was allowed to sit for 1 hour and the solid was collected, washed with water, and dried under vacuum with a nitrogen sweep to afford 1.62 g (83%) of 4p.

$^1$H NMR (CDCl$_3$) δ 7.64 (m, 2H); 7.386 (br s, 4H); 7.25–6.9 (m, 8H); 6.82–6.7 (m, 2H); 6.65–6.5 (m, 2H); 4.95 (m, 1H); 4.534 (br s, 1H); 4.423 (br s, 1H); 4.156 (br s,1H); 3.802 (s, 5H); 2.187 (d, 3H, J=3.57 Hz); 1.521 (d, 3H, J=6.87 Hz).

Example 16

Preparation of N-Acetyl L-phenylalanine methyl ester using the Rhodium complex of Ligand 4a Methyl 2-acetamidocinnamate (110 mg; 0.5 mmol) was dissolved in a reaction vessel in anhydrous tetrahydrofuran (THF, 3.0 mL) and degassed with argon for 15 minutes. Bis(1,5-cyclooctadiene)rhodium trifluoromethanesulfonate (2.3 mg; 5 μmol; 0.01 equiv) and ligand 4a from Example 1 (3.7 mg; 6 μmol; 0.012 equiv) were combined and argon-degassed anhydrous THF (2.0 mL) was added. This solution was stirred at 25° C. under argon for 15 minutes and then added to the solution of methyl 2-acetamidocinnamate. The resulting solution was then flushed with hydrogen and pressurized to 0.69–1.38 barg (10–20 pounds per square inch gauge—psig) hydrogen. The reaction mixture was stirred for 6 hours to afford 100% conversion to N-acetyl L-phenylalanine methyl ester with 99.2% ee as determined by chiral GC analysis.

$^1$H NMR (CD$_3$OD, 400 MHz) δ 7.28–7.16 (m, 5H), 4.64–4.61 (m, 1H), 3.65 (s, 3H), 3.13–3.08 (dd, 1H, J=5.5, 13.9 Hz), 2.94–2.88 (dd, 1H, J=8.9, 13.9 Hz), 1.87 (s, 3H).

Chiral GC conditions: Chirasil L-Valine [Varian] 25 m×0.25 mm ID, film thickness 0.12 μm, 160° C. 9 minutes, 160–185° C. 70° C./minutes, 185° C. 5 min, 15 psig He. $t_R$[(R)-N-acetyl phenylalanine methyl ester] 7.77 min, $t_R$[(S)-N-acetyl phenylalanine methyl ester] 8.29 minutes, $t_R$(methyl 2-acetamidocinnamate) 13.24 minutes.

Example 17

Preparation of N-Acetyl L-phenylalanine using the Rhodium complex of Ligand 4a

2-Acetamidocinnamic acid (102 mg; 0.5 mmol) was dissolved in a reaction vessel in anhydrous methanol (3.0 mL) and degassed with argon for 15 minutes. Bis(1,5cyclooctadiene)rhodium trifluoromethanesulfonate (2.3 mg; 5 μmol; 0.01 equiv) and ligand 4a from Example 1 (3.7 mg; 6 μmol; 0.012 equiv) were combined and argon-degassed anhydrous methanol (2.0 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyidiazomethane (2.0 M in hexane; 60 μL; 0.12 mmol; 5 equiv) by stirring in methanol (1 mL) for 30 minutes. After acetic acid quench, the sample was analyzed by chiral GC to indicate 100% conversion to N-acetyl L-phenylalanine with 99.4% ee.

Example 18

Methyl Lactate using the Rhodium Complex of Ligand 4a

Methyl pyruvate (51 mg; 0.50 mmol) was dissolved in a reaction vessel in anhydrous THF (3.0 mL) and degassed with argon for 15 minutes. Bis(1,5-cycloocta-diene)rhodium trifluoromethanesulfonate (2.3 mg; 5 μmol; 0.01 equiv) and ligand 4a from Example 1 (3.7 mg; 6 μmol; 0.012 equiv) were combined and argon-degassed anhydrous THF (2.0 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 8 hours to afford 90.2% conversion to methyl (R)-lactate with 88.2% ee as determined by chiral GC analysis. The analytical properties of methyl lactate were identical to an authentic sample.

Chiral GC [Cyclosil-B (J&W Scientific) 30 m×0.25 mm ID, film thickness 0.25 μm, 75° C. isothermal, 15 psig He]: $t_R$[methyl (R)-lactate] 7.75 min, $t_R$[methyl (S)-lactate] 9.16 min. $t_R$(methyl pyruvate) 5.16 min.

Example 19

Preparation of N-Acetyl L-phenylalanine methyl ester using the Rhodium complex of Ligand 4b Methyl 2-acetamidocinnamate (110 mg; 0.5 mmol) was dissolved in a reaction vessel in anhydrous tetrahydrofuran (THF, 5.0 mL) and degassed with argon for 15 minutes. Bis(1,5-cyclooctadiene)rhodium trifluoromethanesulfonate (2.3 mg; 5 μmol; 0.01 equiv) and ligand 4b from Example 2 (3.8 mg; 6 μmol; 0.012 equiv) were combined and argon-degassed anhydrous THF (0.5 mL) was added. This solution was stirred at 25° C. under argon for 15 minutes and then added to the solution of methyl 2-acetamidocinnamate. The resulting solution was then flushed with hydrogen and pressurized to 0.69–1.38 barg (10–20 psig) hydrogen. The reaction mixture was stirred for 6 hours to afford 91.1% conversion to N-acetyl L-phenylalanine methyl ester with 91.8% ee as determined by chiral GC analysis.

Example 20

Preparation of R-2-methylsuccinic acid using the Rhodium complex of Ligand 4b

Itaconic acid (65 mg; 0.5 mmol) was dissolved in a reaction vessel in anhydrous methanol (5.0 mL) and degassed with argon for 15 minutes. Bis(1,5 cyclooctadiene) rhodium trifluoromethanesulfonate (2.3 mg; 5 μmol; 0.01 equiv) and ligand 4b from Example 2 (3.8 mg; 6 μmol; 0.012 equiv) were combined and argon-degassed anhydrous methanol (0.50 mL) was added. This solution was stirred at 25° C. under argon for 15 minutes and then added to the solution of itaconic acid. The resulting solution was then flushed with hydrogen and pressurized to 0.69–1.38 barg (10–20 psig) hydrogen. The reaction mixture was stirred for 6 hours at which point a sample (0.024 mmol) was converted to the dimethyl ester by the action of trimethylsilyidiazomethane (2.0 M in hexane; 120 μL; 0.24 mmol; 10 equiv) by stirring in methanol (1 mL) for 30 min. After acetic acid quench, the sample was analyzed by chiral GC to indicate 100% conversion to R-2-methylsuccinic acid with 90.9% ee.

Chiral GC for dimethyl 2-methylsuccinate [Cyclosil-B, J&W Scientific, 30 m×0.25 mm ID, film thickness 0.25 μm, 90° C. isothermal, 15 psig He]: $t_R$[dimethyl (R)-2-methylsuccinate] 17.36 minutes, $t_R$[dimethyl (S)-2-methylsuccinate] 17.82 minutes, $t_R$(dimethyl itaconate) 23.16 minutes.

Example 21

Preparation of N-Acetyl L-alanine using the Rhodium complex of Ligand 4c

2-Acetamidoacrylate (65 mg; 0.5 mmol) was dissolved in a reaction vessel in anhydrous THF (5.0 mL) and degassed with argon for 15 minutes. Bis(1,5-cycloocta-diene)rhodium trifluoromethanesulfonate (2.3 mg; 5 μmol; 0.01 equiv) and ligand 4c from Example 3 (4.0 mg; 6 μmol; 0.012 equiv) were combined and argon-degassed anhydrous THF (0.50 mL) was added. This solution was stirred at 25° C. under argon for 15 minutes and then added to the solution of 2-acetamidoacrylate. The resulting solution was then flushed with hydrogen and pressurized to 0.69–1.38 barg (10–20 psig) hydrogen. The reaction mixture was stirred for 6 hours, at which point a sample (0.024 mmol) was converted to the methyl ester by the action of trimethylsilyidiazomethane (2.0 M in hexane; 60 μL; 0.12 mmol; 5 equiv) by stirring in methanol (1 mL) for 30 min. After acetic acid quench, the sample was analyzed by chiral GC to indicate 14.4% conversion to N-acetyl L-alanine with 93.6% ee.

Chiral GC conditions: Cyclosil-B [J&W Scientific] 30 m×0.25 mm ID, 0.25 μm film thickness, 40–100° C. 70° C./min, 100° C. 15 min, 100–170° C. 15° C./min, 170° C. 7 min, 6 psig He 6 min, 6–20 psig He 80 psig/min, 20 psig 22 min. $t_R$[(R)-N-acetylalanine methyl ester) 19.36 min, $t_R$[(S)-N-acetylalanine methyl ester) 19.12 min, $t_R$(methyl 2-acetamidoacrylate) 17.91 min.

Example 22

Preparation of N-Acetyl L-alanine using the Rhodium complex of Ligand 4d

2-Acetamidoacrylate (65 mg; 0.5 mmol) was dissolved in a reaction vessel in anhydrous THF (5.0 mL) and degassed with argon for 15 minutes. Bis(1,5-cycloocta-diene)rhodium trifluoromethanesulfonate (2.3 mg; 5 μmol; 0.01 equiv) and ligand 4d from Example 4 (3.9 mg; 6 μmol; 0.012 equiv) were combined and argon-degassed anhydrous THF ( 0.50 mL) was added. This solution was stirred at 25° C. under argon for 15 minutes and then added to the solution of 2-acetamidoacrylate. The resulting solution was then flushed with hydrogen and pressurized to 0.69–1.38 barg (10–20 psig) hydrogen. The reaction mixture was stirred for 6 hours, at which point a sample (0.024 mmol) was converted to the methyl ester by the action of trimethylsilyidiazomethane (2.0 M in hexane; 60 μL; 0.12 mmol; 5 equiv) by stirring in methanol (1 mL) for 30 min. After acetic acid quench, the sample was analyzed by chiral GC to indicate 92.6% conversion to N-acetyl L-alanine with 93.4% ee.

Example 23

Preparation of N-Acetyl L-phenylalanine using the Rhodium complex of Ligand 4e

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4e from Example 5 (4.0 mg; 6 μmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 μL; 0.12 mmol; 5 equiv) by stirring in methanol (1 mL) for 30 minutes. After acetic acid quench, the sample was analyzed by chiral GC to indicate 98.8% conversion to N-acetyl L-phenylalanine with 94.0% ee.

Example 24

Preparation of N-Acetyl L-phenylalanine using the Rhodium complex of Ligand 4f

2-Acetamidocinnamic acid (102 mg; 0.5 mmol) was dissolved in a reaction vessel in anhydrous methanol (5.0 mL) and degassed with argon for 15 minutes. Bis(1, 5cyclooctadiene)rhodium trifluoromethanesulfonate (2.3 mg; 5 μmol; 0.01 equiv) and ligand 4f from Example 6 (4.1 mg; 6 μmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 μL; 0.12 mmol; 5 equiv) by stirring in methanol (1 mL) for 30 minutes. After acetic acid quench, the sample was analyzed by chiral GC to indicate 98.8% conversion to N-acetyl L-phenylalanine with 93.4% ee.

Example 25

Preparation of N-Acetyl L-alanine methyl ester using the Rhodium complex of Ligand 4g Methyl 2-acetamidoacrylate (72 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4g from Example 7 (4.2 mg; 6 μmol; 0.012 equiv) were combined and argon-degassed anhydrous methanol (0.50 mL) was added. This solution was stirred at 25° C. under argon for 15 minutes and then added to the solution of methyl 2-acetamidoacrylate. The resulting solution was then flushed with hydrogen and pressurized to 0.69–1.38 barg (10–20 psig) hydrogen. The reaction mixture was stirred for 6 hours, and the reaction mixture was analyzed by chiral GC to indicate 99.4% conversion to N-acetyl L-alanine methyl ester with 96.2% ee.

$^1$H NMR (CD$_3$OD, 600MHz) δ 4.42–4.38 (dd, 1H, J=7.3, 14.7 Hz); 3.72 (s, 3H); 1.98 (s, 3H); 1.38–1.37 (d, 3H, J=7.3 Hz). Chiral GC conditions: Cyclosil-B [J&W Scientific] 30 m×0.25 mm ID, 0.25 μm film thickness, 40–100° C. 70° C./min, 100° C. 15 min, 100–170° C. 15° C./min, 170° C. 7 min, 6 psig He 6 min, 6–20 psig He 80 psig/min, 20 psig 22 min, $t_R$[(R)-N-acetylalanine methyl ester) 19.36 min, $t_R$[(S)-N-acetylalanine methyl ester) 19.12 min, $t_R$(methyl 2-acetamidoacrylate) 17.91 min.

Example 26

Preparation of N-Acetyl L-phenylalanine using the Rhodium complex of Ligand 4h

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4h from Example 8 (4.2 mg; 6 μmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 μL; 0.12 mmol; 5 equiv) by stirring in methanol (1 mL) for 30 minutes. After acetic acid quench, the sample was analyzed by chiral GC to indicate 98.9% conversion to N-acetyl L-phenylalanine with 86.0% ee.

Example 27

Preparation of N-Acetyl L-phenylalanine methyl ester using the Rhodium complex of Ligand 4i Methyl 2-acetamidocinnamate (110 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4i from Example 9 (4.0 mg; 6 μmol; 0.012 equiv) were combined and argon-degassed anhydrous methanol (0.5 mL) was added. This solution was stirred at 25° C. under argon for 15 minutes and then added to the solution of methyl 2-acetamidocinnamate. The resulting solution was then flushed with hydrogen and pressurized to 0.69–1.38 bars gauge (10–20 psig) hydrogen. The reaction mixture was stirred for 6 hours to afford 100% conversion to N-acetyl L-phenylalanine methyl ester with 97.8% ee as determined by chiral GC analysis.

Example 28

Preparation of N-tert-Butoxycarbonyl L-cyclopropylalanine benzyl ester using the Rhodium complex of Ligand 4i Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4i from Example 9 (4.0 mg; 6 μmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 100% conversion to amino acid derivative benzyl (S)-2-tert-butoxycarbonylamino-3-cyclopropylpropionate with 98.1 % ee as determined by chiral GC analysis.

$^1$H NMR (CDCl$_3$, 300 MHz) δ 7.37–7.26 (m, 5H), 6.07–6.04 (d, 1H, J=10.8 Hz), 5.92 (bs, 1H), 5.18 (s, 2H), 1.76–1.66 (m, 1H), 1.45 (s, 9H), 1.03–0.97 (s, 2H), 0.66–0.63 (m, 2H). Chiral GC [Chirasil L-Valine (Varian) 25 m×0.25 mm ID, film thickness 0.12 μm, 175° C. isothermal, 15 psig He]: t$_R$[benzyl (R)-2-tert-butoxyaminocarbonyl-3-cyclopropylpropionate] 14.59 minutes, t$_R$[benzyl (S)-2-tert-butoxycarbonylamino-3-cyclopropylpropionate] 15.21 minutes, t$_R$(benzyl 2-tert-butoxycarbonylamino-3-cyclopropylacrylate) 26.34 minutes.

Example 29

Preparation of N-Acetyl L-phenylalanine using the Rhodium complex of Ligand 4i

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4i from Example 9 (4.0 mg; 6 μmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 μL; 0.12 mmol; 5 equiv) by stirring in methanol (1 mL) for 30 minutes. After acetic acid quench, the sample was analyzed by chiral GC to indicate 99.5% conversion to N-acetyl L-phenylalanine with 98.3% ee.

Example 30

Preparation of R-2-methylsuccinic acid using the Rhodium complex of Ligand 4i

Itaconic acid (65 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4i from Example 9 (4.0 mg; 6 μmol; 0.012 equiv) were combined and argon-degassed anhydrous methanol (0.50 mL) was added. This solution was stirred at 25° C. under argon for 15 minutes and then added to the solution of itaconic acid. The resulting solution was then flushed with hydrogen and pressurized to 0.69–1.38 barg (10–20 psig) hydrogen. The reaction mixture was stirred for 6 hours at which point a sample (0.024 mmol) was converted to the dimethyl ester by the action of trimethylsilyldiazomethane (2.0 M in hexane; 120 μL; 0.24 mmol; 10 equiv) by stirring in methanol (1 mL) for 30 minutes. After acetic acid quench, the sample was analyzed by chiral GC to indicate 100% conversion to (R)-2-methylsuccinic acid with 94.1 % ee.

Example 31

Preparation of N-Acetyl L-phenylalanine methyl ester using the Rhodium complex of Ligand 4j Methyl 2-acetamidocinnamate (110 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4j from Example 10 (4.1 mg; 6 μmol; 0.012 equiv) were combined and argon-degassed anhydrous methanol (0.5 mL) was added. This solution was stirred at 25° C. under argon for 15 minutes and then added to the solution of methyl 2-acetamidocinnamate. The resulting solution was then flushed with hydrogen and pressurized to 0.69–1.38 barg (10–20 psig) hydrogen. The reaction mixture was stirred for 6 hours to afford 100% conversion to N-acetyl L-phenylalanine methyl ester with 99.0% ee as determined by chiral GC analysis.

Example 32

Preparation of N-tert-Butoxycarbonyl L-cyclopropylalanine benzyl ester using the Rhodium complex of Ligand 4j Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5cyclooctadiene) rhodium trifluoromethanesulfonate (2.3 mg; 5 μmol; 0.01 equiv) and ligand 4j from Example 10 (4.1 mg; 6 μmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 99.6% conversion to amino acid derivative benzyl (S)-2-tert-butoxycarbonylamino-3-cyclopropylpropionate with 99.4% ee as determined by chiral GC analysis.

Example 33

Preparation of R-2-methylsuccinic acid using the Rhodium complex of Ligand 4j

Itaconic acid (65 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4j from Example 10 (4.1 mg; 6 μmol; 0.012 equiv) were combined and argon-degassed anhydrous methanol (0.50 mL) was added. This solution was stirred at 25° C. under argon for 15 minutes and then added to the solution of itaconic acid. The resulting solution was then flushed with hydrogen and pressurized to 0.69–1.38 bars gauge (10–20 psig) hydrogen. The reaction mixture was stirred for 6 hours at which point a sample (0.024 mmol) was converted to the dimethyl ester by the action of trimethylsilyldiazomethane (2.0 M in hexane; 120 μL; 0.24 mmol; 10 equiv) by stirring in methanol (1 mL) for 30 min. After acetic acid quench, the sample was analyzed by chiral GC to indicate 99.9% conversion to (R)-2-methylsuccinic acid with 98.4% ee.

Example 34

Preparation of N-Acetyl L-phenylalanine using the Rhodium complex of Ligand 4k

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 µmol; 0.01 equiv) and ligand 4k from Example 11 (4.5 mg; 6 µmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 µL; 0.12 mmol; 5 equiv) by stirring in methanol (1 mL) for 30 minutes. After acetic acid quench, the sample was analyzed by chiral GC to indicate 99.6% conversion to N-acetyl L-phenylalanine with 99.2% ee.

Example 35

Preparation of N-tert-Butoxycarbonyl L-cyclopropylalanine benzyl ester using the Rhodium complex of Ligand 4k Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 µmol; 0.01 equiv) and ligand 4k from Example 11 (4.5 mg; 6 µmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 99.9% conversion to amino acid derivative benzyl (S)-2-tert-butoxycarbonylamino-3-cyclopropylpropionate with 98.8% ee as determined by chiral GC analysis.

Example 36

Preparation of N-Acetyl L-phenylalanine using the Rhodium complex of Ligand 4m

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 µmol; 0.01 equiv) and ligand 4m from Example 12 (4.1 mg; 6 µmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanie methyl ester by the action of trimethylsilyldiazomethane (2.0 M in hexane; 60 µL; 0.12 mmol; 5 equiv) by stirring in methanol (1 mL) for 30 minutes. After acetic acid quench, the sample was analyzed by chiral GC to indicate 99.5% conversion to N-acetyl L-phenylalanine with 99.1% ee.

Example 37

Preparation of N-tert-Butoxycarbonyl L-cyclopropylalanine benzyl ester using the Rhodium complex of Ligand 4m Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 µmol; 0.01 equiv) and ligand 4m from Example 12 (4.1 mg; 6 µmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 100% conversion to amino acid derivative benzyl (S)-2-tert-butoxycarbonylamino-3-cyclopropylpropionate with 99.2% ee as determined by chiral GC analysis.

Example 38

Preparation of N-Acetyl L-phenylalanine using the Rhodium complex of Ligand 4n

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 µmol; 0.01 equiv) and ligand 4n from Example 13 (4.5 mg; 6 µmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 µL; 0.12 mmol; 5 equiv) by stirring in methanol (1 mL) for 30 minutes. After acetic acid quench, the sample was analyzed by chiral GC to indicate 99.6% conversion to N-acetyl L-phenylalanine with 98.8% ee.

Example 39

Preparation of N-tert-Butoxycarbonyl L-cyclopropylalanine benzyl ester using the Rhodium complex of Ligand 4n Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 µmol; 0.01 equiv) and ligand 4n from Example 13 (4.5 mg;

6 μmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 99.5% conversion to amino acid derivative benzyl (S)-2-tert-butoxycarbonylamino-3-cyclopropylpropionate with 98.8% ee as determined by chiral GC analysis.

Example 40

Preparation of N-Acetyl L-phenylalanine using the Rhodium complex of Ligand 4o

2-Acetamidocinnamic acid (102 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4o from Example 14 (3.9 mg; 6 μmol; 0.012 equiv) were combined and argon-degassed anhydrous methanol (0.50 mL) was added. This solution was stirred at 25° C. under argon for 15 minutes and then added to the solution of 2-acetamidocinnamic acid. The resulting solution was then flushed with hydrogen and pressurized to 0.69–1.38 bars gauge (10–20 psig) hydrogen. The reaction mixture was stirred for 6 hours, at which point a sample (0.024 mmol) was converted to N-acetyl L-phenylalanine methyl ester by the action of trimethylsilyldiazomethane (2.0 M in hexane; 60 μL; 0.12 mmol; 5 equiv) by stirring in methanol (1 mL) for 30 minutes. After acetic acid quench, the sample was analyzed by chiral GC to indicate 99.5% conversion to N-acetyl L-phenylalanine with 98.8% ee.

Example 41

Preparation of N-tert-Butoxycarbonyl L-cyclopropylalanine benzyl ester using the Rhodium complex of Ligand 4o Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4o from Example 14 (3.9 mg; 6 μmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 100% conversion to amino acid derivative benzyl (S)-2-tert-butoxycarbonylamino-3-cyclopropylpropionate with 98.8% ee as determined by chiral GC analysis.

Example 42

Preparation of N-Acetyl L-phenylalanine methyl ester using the Rhodium complex of Ligand 4p Methyl 2-acetamidocinnamate (110 mg; 0.5 mmol) was dissolved in a reaction vessel in anhydrous methanol (5.0 mL) and degassed with argon for 15 minutes. Bis(1,5-cyclooctadiene)rhodium trifluoromethanesulfonate (2.3 mg; 5 μmol; 0.01 equiv) and ligand 4p from Example 15 (3.9 mg; 6 μmol; 0.012 equiv) were combined and argon-degassed anhydrous methanol (0.5 mL) was added. This solution was stirred at 25° C. under argon for 15 minutes and then added to the solution of methyl 2-acetamidocinnamate. The resulting solution was then flushed with hydrogen and pressurized to 0.69–1.38 bars gauge (10–20 psig) hydrogen. The reaction mixture was stirred for 6 hours to afford 100% conversion to N-acetyl L-phenylalanine methyl ester with 98.8% ee as determined by chiral GC analysis.

Example 43

Preparation of N-tert-Butoxycarbonyl L-cyclopropylalanine benzyl ester using the Rhodium complex of Ligand 4p Benzyl 2-tert-butoxycarbonylamino-3-cyclopropylacrylate (159 mg; 0.5 mmol) was dissolved in a reaction vessel in anhydrous methanol (5.0 mL) and degassed with argon for 15 minutes. Bis(1,5cyclooctadiene) rhodium trifluoromethanesulfonate (2.3 mg; 5 μmol; 0.01 equiv) and ligand 4p from Example 15 (3.9 mg; 6 μmol; 0.012 equiv) were combined and argon-degassed anhydrous methanol (0.5 mL) was added. This solution was stirred at 25° C. under argon for 15 minutes and then added to the solution of benzyl 2-tert-butoxycarbonylamino-3-cyclopropylacrylate. The resulting solution was then flushed with hydrogen and pressurized to 0.69–1.38 barg (10–20 psig) hydrogen. The reaction mixture was stirred for 6 hours to afford 100% conversion to amino acid derivative benzyl (S)-2-tert-butoxycarbonylamino-3cyclopropylpropionate with 99.0% ee as determined by chiral GC analysis.

The invention has been described in detail with particular reference to preferred embodiments thereof, but it will be understood that variations and modifications can be effected within the spirit and scope of the invention.

I claim:

1. Process for the preparation of a phosphine-aminophosphine compound having formula 1

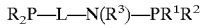

$$R_2P—L—N(R^3)—PR^1R^2 \quad\quad 1$$

which comprises (1) contacting a compound having formula 2

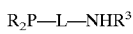

$$R_2P—L—NHR^3 \quad\quad 2$$

with phosphorus trihalide $PX_3$ in the presence of an inert, organic solvent and an acid acceptor to produce intermediate compound having formula 3

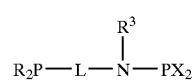

$$R_2P—L—\overset{R^3}{\underset{|}{N}}—PX_2 \quad\quad 3$$

and (2) contacting intermediate compound 3 with a reactant having the formula $R^1—M^1$, $R^2—M^1$ or a mixture thereof;

wherein

R, $R^1$, $R^2$, and $R^3$ are, independently, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, or oxygen;

L is a divalent chiral radical selected from substituted or unsubstituted, branched- or straight-chain $C_1$–$C_{20}$ alkylene, substituted or unsubstituted $C_3$–$C_8$ cycloalkylene, substituted or unsubstituted $C_6$–$C_{20}$ carbocyclic arylene, substituted or unsubstituted $C_4$–$C_{20}$ heteroarylene having one to three heteroatoms wherein the heteroatoms are selected from sulfur, nitrogen, and oxygen, or substituted or unsubstituted metallocenylmethylene, wherein L is substantially enantiomerically pure, X is halide; and $M^1$ is a metal selected from Group I or Group II.

2. Process according to claim 1 wherein steps (1) and (2) are carried out in the presence of an inert, organic solvent selected from cyclic and acyclic ethers, aromatic hydrocarbons, aliphatic and alicyclic hydrocarbons and mixtures of any two or more thereof at a temperature in the range of about –100° C. to about the boiling point of the inert, organic solvent.

3. Process according to claim 1 for the preparation of a phosphine-aminophosphine compound having formula 4

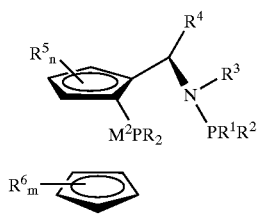

which comprises (1) contacting a compound having the formula

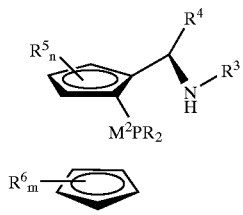

with phosphorus trihalide $PX_3$ in the presence of an acid acceptor to produce intermediate compound having the formula

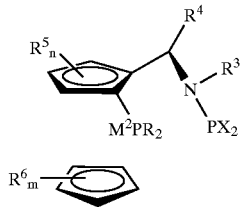

and (2) contacting the intermediate compound with a reactant having the formula $R^1$—$M^1$, $R^2$—$M^1$ or a mixture thereof;

wherein $R^4$, $R^5$, and $R^6$ are independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6$–$C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

n is 0 to 3;

m is 0 to 5; and $M^2$ is selected from the metals of Groups IVB, VB, VIB, VIIB and VIII; and wherein steps (1) and (2) are carried out in the presence of an inert, organic solvent selected from cyclic and acyclic ethers, aromatic hydrocarbons, aliphatic and alicyclic hydrocarbons or mixtures of any two or more thereof at a temperature of about –100° C. to about the boiling point of the inert, organic solvent.

4. Process according to claim 3 wherein the solvent is diethyl ether, diisopropyl ether, tert-butyl methyl ether, tetrahydrofuran, benzene, toluene, xylene, hexane, heptane, cyclohexane and/or mixtures of any two or more thereof and the temperature is about –80° C. to 60° C.

5. Process according to claim 3 wherein the acid acceptor is a $C_3$–$C_{15}$ tertiary amine or pyridine and X is Cl; the solvent is diethyl ether, diisopropyl ether, tert-butyl methyl ether, tetrahydrofuran, benzene, toluene, xylene, hexane, heptane, cyclohexane or mixtures of any two or more thereof; and the temperature is about –80° C. to 60° C.

6. Process according to claim 3 wherein the acid acceptor is a $C_3$–$C_{15}$ tertiary amine or pyridine, X is Cl, $M^1$ is MgBr, MgCl, MgI, Li, Na, or K, the solvent is diethyl ether, diisopropyl ether, tert-butyl methyl ether, tetrahydrofuran, benzene, toluene, xylene, hexane, heptane, cyclohexane or mixtures of any two or more thereof and the temperature is about –80° C. to 60° C.

7. Process according to claim 3 wherein the acid acceptor is a $C_3$–$C_{15}$ tertiary amine or pyridine, X is Cl; $M^1$ is MgBr, MgCl, MgI, Li, Na, or K; the solvent is diethyl ether, diisopropyl ether, tert-butyl methyl ether, tetrahydrofuran, benzene, toluene, xylene, hexane, heptane, cyclohexane or mixtures of any two or more thereof; the temperature is about –80° C. to 60° C.; R is aryl; $R^1$ and $R^2$ are the same and are aryl, $C_2$–$C_6$ alkyl, or $C_3$–$C_6$ cycloalkyl; $R^3$ is hydrogen, $C_1$ to $C_6$ alkyl, or aryl; $R^4$ is hydrogen, $C_1$ to $C_6$ alkyl, benzyl, racemic or substantially enantiomerically pure 1-phenylethyl, or aryl; $R^5$ and $R^6$ are hydrogen; and $M^2$ is iron, ruthenium, or osmium.

8. Process according to claim 3 wherein the acid acceptor is triethylamine; the solvent is toluene; $M^1$ is MgBr or MgCl, R is phenyl; $R^1$ and $R^2$ are the same and are phenyl, p-methoxyphenyl, 3,4-difluorophenyl, 3,5-difluorophenyl, 3,4-dichlorophenyl, 3,5-dichlorophenyl, 3-fluorophenyl, or 4-fluorophenyl; $R^3$ is hydrogen, $C_1$ to $C_6$ alkyl, or aryl; $R^4$ is hydrogen, $C_1$ to $C_6$ alkyl, benzyl, racemic or substantially enantiomerically pure 1-phenylethyl, or aryl; $R^5$ and $R^6$ are hydrogen; and $M^2$ is iron.

9. Process according to claim 1 for the preparation of a phosphine-aminophosphine compound having formula 5

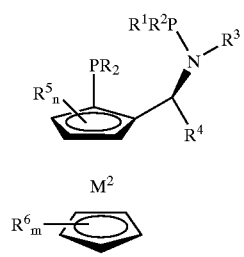

which comprises (1) contacting a compound having the formula

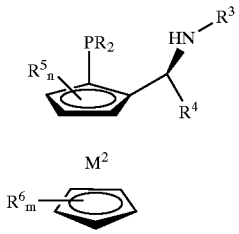

with phosphorus trihalide $PX_3$ in the presence of an acid acceptor to produce intermediate compound having the formula

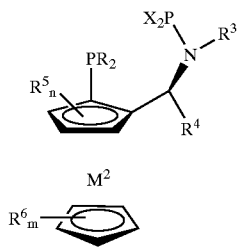

and (2) contacting the intermediate compound with a reactant having the formula $R^1$—$M^1$, $R^2$—$M^1$ or a mixture thereof;

wherein $R^4$, $R^5$, and $R^6$ are, independently, hydrogen, substituted or unsubstituted, branched- or straight-chain $C_1$–$C_{20}$ alkyl, substituted or unsubstituted $C_3$–$C_8$ cycloalkyl, substituted or unsubstituted $C_6C_{20}$ carbocyclic aryl, or substituted or unsubstituted $C_4$–$C_{20}$ heteroaryl having one to three heteroatoms wherein the heteroatoms are selected from sulfur, nitrogen, and oxygen;

n is 0 to 3;

m is 0 to 5; and $M^2$ is selected from the metals of Groups IVB, VB, VIB, VIIB and VIII; and wherein steps (1) and (2) are carried out in the presence of an inert, organic solvent selected from cyclic and acyclic ethers, aromatic hydrocarbons, aliphatic and alicyclic hydrocarbons or mixtures of any two or more thereof at a temperature of about −100° C. to the boiling point of the solvent.

10. Process according to claim 9 wherein the solvent is diethyl ether, diisopropyl ether, tert-butyl methyl ether, tetrahydrofuran, benzene, toluene, xylene, hexane, heptane, cyclohexane or mixtures of any two or more thereof, and the temperature is about −80° C. to 60° C.

11. Process according to claim 9 wherein the acid acceptor is a $C_3$–$C_{15}$ tertiary amine or pyridine; X is Cl; the solvent is diethyl ether, diisopropyl ether, tert-butyl methyl ether, tetrahydrofuran, benzene, toluene, xylene, hexane, heptane, cyclohexane or mixtures of any two or more thereof; and the temperature is about −80° C. to 60° C.

12. Process according to claim 9 wherein the acid acceptor is a $C_3$–$C_{15}$ tertiary amine or pyridine; X is Cl; $M^1$ is MgBr, MgCl, MgI, Li, Na, or K; the solvent is diethyl ether, diisopropyl ether, tert-butyl methyl ether, tetrahydrofuran, benzene, toluene, xylene, hexane, heptane, cyclohexane or mixtures of any two or more thereof; and the temperature is about −80° C. to 60° C.

13. Process according to claim 9 wherein the acid acceptor is a $C_3$–$C_{15}$ tertiary amine or pyridine; X is Cl; $M^1$ is MgBr, MgCl, MgI, Li, Na, or K; the solvent is diethyl ether, diisopropyl ether, tert-butyl methyl ether, tetrahydrofuran, benzene, toluene, xylene, hexane, heptane, cyclohexane or mixtures of any two or more thereof; the temperature is about −80° C. to 60° C.; R is aryl; $R^1$ and $R^2$ are the same and are aryl, $C_2$–$C_6$ alkyl, or $C_2C_6$ cycloalkyl, $R^3$ is hydrogen, $C_1$ to $C_6$ alkyl, or aryl; $R^4$ is hydrogen, $C_1$ to $C_6$ alkyl, benzyl, racemic or substantially enantiomerically pure 1-phenylethyl, or aryl; $R^5$ and $R^6$ are hydrogen; and $M^2$ iron, ruthenium, or osmium.

14. Process according to claim 9 wherein the acid acceptor is triethylamine; the solvent is toluene; $M^1$ is MgBr or MgCl; R is phenyl; $R^1$ and $R^2$ are the same and are phenyl, p-methoxyphenyl, 3,4-difluorophenyl, 3,5difluorophenyl, 3,4-dichlorophenyl, 3,5-dichlorophenyl, 3-fluorophenyl, or 4-fluorophenyl; $R^3$ is hydrogen, $C_1$ to $C_6$ alkyl, or aryl; $R^4$ is hydrogen, $C_1$ to $C_6$ alkyl, benzyl, racemic or substantially enantiomerically pure 1-phenylethyl, or aryl; $R^5$ and $R^6$ are hydrogen; and $M^2$ is iron.

* * * * *